United States Patent
Sun et al.

(12) 
(10) Patent No.: US 6,184,437 B1
(45) Date of Patent: Feb. 6, 2001

(54) LYSINE RICH PROTEIN FROM WINGED BEAN

(75) Inventors: Samuel S. M. Sun; Liwen Xiong, both of Honolulu, HI (US); Yuxiang Jing; Bolin Liu, both of Beijing (CN)

(73) Assignees: Beijing Vegetable Research Center; Institute of Botany, Academia Sinica, both of Beijing (CN); University of Hawaii, Honolulu, HI (US)

( * ) Notice: Under 35 U.S.C. 154(b), the term of this patent shall be extended for 0 days.

(21) Appl. No.: 08/964,722

(22) Filed: Nov. 5, 1997

Related U.S. Application Data (63) Continuation of application No. 08/804,783, filed on Feb. 24, 1997, now abandoned, which is a continuation of application No. 08/697,309, filed on Feb. 22, 1996, now abandoned.
(60) Provisional application No. 60/002,918, filed on Aug. 29, 1995, and provisional application No. 60/004,266, filed on Sep. 25, 1995.

(51) Int. Cl.[7] .............................. A01H 1/00; C07H 21/00; C07K 14/415; C12N 5/14
(52) U.S. Cl. ..................... 800/278; 800/292; 800/293; 800/281; 435/410; 435/69.1; 435/71.1; 435/91.4; 435/419; 435/320.1; 530/350; 530/370; 536/23.1; 536/23.6; 536/24.1
(58) Field of Search .................... 800/278, 292, 800/293, 281; 435/410, 69.1, 71.1, 91.4, 419, 320.1; 530/350, 370; 536/23.1, 23.6, 24.1

(56) References Cited

U.S. PATENT DOCUMENTS 5,559,223 * 9/1996 Falco et al. .

FOREIGN PATENT DOCUMENTS 94 16078    7/1994   (WO) .
95 15392    6/1995   (WO) .

OTHER PUBLICATIONS

Peyachoknagul et al. Plant Molecular Biology, vol. 12, 1989 p. 51–58.*
Yamamoto et al. J. Biochem., vol. 94, 1983, p. 849–863.*
Kortt et al. Eur. J. Biochem., vol. 181, 1989, p 403–408.*
Liu B et al., "Screening of lysine–rich plant species and identification of the purified proteins", Chemical Abstracts, vol. 35, No. 1, 1993, pp. 62–68.
Ausubel FM, "Using synthetic oligonucleotides as probes", Current Protocols in Molecular Biology, vol. 1, 1988, pp. 6.4.01–6.4.10.
Crowell D N et al., "Characterization of a 1,2 stress induced, developmentally regulated gene family from soybean", Plant Molecular Biology, vol. 18, Feb. 1992, pp. 459–466.
Walter M H et al., "Bean pathogenesis–related (PR) proteins deduced from elicitor–induced transcripts are members of a ubiquitours new class of conserved PR proteins including pollen allergens", Molecular and General Genetics, vol. 222, Jul. 1990, pp. 353–360.
Liu B et al., Screening of lysine–rich plant species and identification of the purified proteins, ZHIWU XUEBAO, vol. 35, No. 1, 1993, pp. 62–68.

* cited by examiner

Primary Examiner—Phuong T. Bui
(74) Attorney, Agent, or Firm—Morrison & Foerster LLP (57) ABSTRACT

A lysine-rich protein gene has been cloned from winged bean, *Psophocarpus tetragonolobus*, and its DNA sequence and deduced protein sequence are provided. Methods for transforming plant cells are provided that mature into plants having elevated levels of lysine in their seeds.

18 Claims, 4 Drawing Sheets cDNA SEQUENCE OF WB 18-KD SEED PROTEIN

```
  1  GGCACGAGCG GCACGAGGCA AAATCTCTTT CTCAAATCAA CGTTATTTTT
 51  CCATTTCTAT TTGTAATTTG ATCATTATGG GTGTTTTCAC ATATGAGGAT
101  GAAACCACTT CACCAGTGGC TCCTGCTATC CTTTACAAAG CAATAGTTAA
151  AGATGCTGAT AACATCTTTC CAAAGGCTGT TGATTCCTTT AAGAGTGTTG
201  AAATTGTTGA GGGAAATGGT GGTCCTGGAA CCATCAAGAA GATCTCTTTT
251  GTTGAGGATG GGGAAAGCAA GTTGTGTTG CACAAGATTG AGTCAATTGA
301  TGAGGCTAAT TTGGGATACA GCTACAGCAT AGTTGGTGGT GCTGCTTTGC
351  CAGACACAGT GGAGAAGATT ACATTTGAGT CCAAATTGAG TGCTGGACCT
401  TCTGGGAGCT CTGTTGGGAA ACTCACTGTG AAATACCAAA CCAAAGGAGA
451  TGCTGAGCCC AATGAAGAGG AACTCAAAGT TGGCAAAGCC AAGGGTGATG
501  CTCTCTTCAA GGCTGTTGAG GCTTACCTTT TGGCCCATCC TGAATACAAT
551  TGATATCATA TCAACCATAA TCCAATTTCC AATTCAACTT AATCACACTC
601  AGATGATTAT CATTATATGA TCTCAAATTA TACCCTATGG AATGAATCAT
651  ATATGATATC AGTTTATTAA GGTTTTTCAG GAGAGTTTTG TTGGTTTGCA
701  ATGTTGTCCT GTGTGCTCAA GTTGGCTTTC AGTGTAATAA TAAGTCCATG
751  TTCATTGGAT TGAAGTATTT TATAAACTGA AGTTTGATGA AAAAAAAA
```

*FIG. 1*

DEDUCED AMINO ACID SEQUENCE OF cDNA ENCODING WB 18-KDSEED PROTEIN

Met-Gly-Val-Phe-Thr-Tyr-Glu-Asp-Glu-Thr-Thr-Ser-Pro-Val-Ala-
Pro-Ala-Ile-Leu-Tyr-Lys-Ala-Ile-Val-Lys-Asp-Ala-Asp-Asn-Ile
Phe-Pro-Lys-Ala-Val-Asp-Ser-Phe-Lys-Ser-Val-Glu-Ile-Val-Glu
Gly-Asn-Gly-Gly-Pro-Gly-Thr-Ile-Lys-Lys-Ile-Ser-Phe-Val-Glu
Asp-Gly-Glu-Ser-Lys-Phe-Val-Leu-His-Lys-Ile-Glu-Ser-Ile-Asp
Glu-Ala-Asn-Leu-Gly-Tyr-Ser-Tyr-Ser-Ile-Val-Gly-Gly-Ala-Ala
Leu-Pro-Asp-Thr-Val-Glu-Lys-Ile-Thr-Phe-Glu-Ser-Lys-Leu-Ser
Ala-Gly-Pro-Ser-Gly-Gly-Ser-Val-Gly-Lys-Leu-Thr-Val-Lys-Tyr
Gln-Thr-Lys-Gly-Asp-Ala-Glu-Pro-Asn-Glu-Glu-Glu-Leu-Lys-Val
Gly-Lys-Ala-Lys-Glu-Asp-Ala-Leu-Phe-Lys-Ala-Val-Glu-Ala-Tyr
Leu-Leu-Ala-His-Pro-Glu-Tyr-Asn

*FIG. 2* cDNA and DEDUCED AMINO ACID SEQUENCES OF THE 18-KD WB SEED PROTEIN

```
AATTCGGCACGAGGGCACGAGGCAAAATCTCTTTCTCAAATCAACGTTATTTTCCAT                  59
TTCTATTTGTAATTTGATCATT ATG GGT GTT TTC ACA TAT GAG GAT GAA                 104
                       Met Gly Val Phe Thr Tyr Glu Asp Glu
                        1                  5

ACC ACT TCA CAT GTG GCT CCT ATC CTT TAC AAA GCA ATA GTT                    153
Thr-Thr-Ser-Pro-Val-Ala-Pro-Ala-Ile-Leu-Tyr-Lys-Ala-Ile-Val
 10                  15                  20

AAA GAT GCT GAT AAC ATC TTT CCA AAG GCT GTT GAT TCC TTT AAG                198
Lys-Asp-Ala-Asp-Asn-Ile-Phe-Pro-Lys-Ala-Val-Asp-Ser-Phe-Lys
 25                  30                  35

AGT GTT GAA ATT GTT GAG GGA AAT GGT GGT CCT GGA ACC ATC AAG                243
Ser-Val-Glu-Ile-Val-Glu-Gly-Asn-Gly-Gly-Pro-Gly-Thr-Ile-Lys
 40                  45                  50

AAG ATC TCT TTT GTT GAG GAT GGG GAA AGC AAG TTT GTG TTG CAC                288
Lys-Ile-Ser-Phe-Val-Glu-Asp-Gly-Glu-Ser-Lys-Phe-Val-Leu-His
 55                  60                  65

AAG ATT GAG TCA ATT GAT GAG GCT AAT TTG GGA TAC AGC TAC AGC                333
Lys-Ile-Glu-Ser-Ile-Asp-Glu-Ala-Asn-Leu-Gly-Tyr-Ser-Tyr-Ser
 70                  75                  80
```

FIG.3A

```
ATA GTT GGT GGT GCT GCT TTG CCA GCA ACA GTG GAG AAG ATT ACA    378
Ile-Val-Gly-Gly-Ala-Ala-Leu-Pro-Asp-Thr-Val-Glu-Lys-Ile-Thr
 85                      90                      95

TTT GAG TCC AAA TTG AGT GCT GGA CCT TCT GGA GGC TCT GTT GGG    423
Phe-Glu-Ser-Lys-Leu-Ser-Ala-Gly-Pro-Ser-Gly-Gly-Ser-Val-Gly
100                     105                     110

AAA CTC ACT GTG AAA TAC CAA ACC AAA GGA GAT GCT GAG CCC AAT    468
Lys-Leu-Thr-Val-Lys-Tyr-Gln-Thr-Lys-Gly-Asp-Ala-Glu-Pro-Asn
115                     120                     125

GAA GAG CTC AAA GTT GGC AAA GCC AAG GGT GAT GCT CTC TTC        513
Glu-Glu-Leu-Lys-Val-Gly-Lys-Ala-Lys-Gly-Asp-Ala-Leu-Phe
130                     135                     140

AAG GCT GTT GAG GCT TAC CTT TTG GCC CAT CCT GAA TAC AAT TGA    558
Lys-Ala-Val-Glu-Ala-Tyr-Leu-Leu-Ala-His-Pro-Glu-Tyr-Asn
145                     150                     155       158

TATCATATATCAACCATAATCCAATTCCAATTCAACTTAATCACACTCAGATGATTATCA   617
TTATATGATACCCTATGGTCTCAAATTAAATGAATCATATATGATATCAGTTTATTAAG   676
GTTTTTCAGGAGAGTTTGTTTGTTTGCAATGTGTCCTGTGTGCTGAAGTTGGCTTTC     735
AGTGTAATTAATAAGTCCATGTTCATTGGATTGAAGTATTTTATAAACTGAAGTTTGAT   794
GAAAAAAAAA
```

FIG. 3B

SEQUENCE LISTING

```
<160> NUMBER OF SEQ ID NOS: 7

<210> SEQ ID NO 1
<211> LENGTH: 805
<212> TYPE: DNA
<213> ORGANISM: winged bean
<220> FEATURE:
<221> NAME/KEY: CDS
<222> LOCATION: (82)..(555)

<400> SEQUENCE: 1
aattcggcac gagcggcacg aggcaaaatc tctttctcaa atcaacgtta tttttccatt      60
tctatttgta atttgatcat t atg ggt gtt ttc aca tat gag gat gaa acc       111
                        Met Gly Val Phe Thr Tyr Glu Asp Glu Thr
```

-continued

```
                 1               5                   10
act tca cat gtg gct cct gct atc ctt tac aaa gca ata gtt aaa gat    159
Thr Ser His Val Ala Pro Ala Ile Leu Tyr Lys Ala Ile Val Lys Asp
                15                  20                  25 gct gat aac atc ttt cca aag gct gtt gat tcc ttt aag agt gtt gaa    207
Ala Asp Asn Ile Phe Pro Lys Ala Val Asp Ser Phe Lys Ser Val Glu
             30                  35                  40 att gtt gag gga aat ggt ggt cct gga acc atc aag aag atc tct ttt    255
Ile Val Glu Gly Asn Gly Gly Pro Gly Thr Ile Lys Lys Ile Ser Phe
         45                  50                  55 gtt gag gat ggg gaa agc aag ttt gtg ttg cac aag att gag tca att    303
Val Glu Asp Gly Glu Ser Lys Phe Val Leu His Lys Ile Glu Ser Ile
     60                  65                  70 gat gag gct aat ttg gga tac agc tac agc ata gtt ggt ggt gct gct    351
Asp Glu Ala Asn Leu Gly Tyr Ser Tyr Ser Ile Val Gly Gly Ala Ala
 75                  80                  85                  90 ttg cca gca aca gtg gag aag att aca ttt gag tcc aaa ttg agt gct    399
Leu Pro Ala Thr Val Glu Lys Ile Thr Phe Glu Ser Lys Leu Ser Ala
                 95                 100                 105 gga cct tct gga ggc tct gtt ggg aaa ctc act gtg aaa tac caa acc    447
Gly Pro Ser Gly Gly Ser Val Gly Lys Leu Thr Val Lys Tyr Gln Thr
             110                 115                 120 aaa gga gat gct gag ccc aat gaa gag gaa ctc aaa gtt ggc aaa gcc    495
Lys Gly Asp Ala Glu Pro Asn Glu Glu Glu Leu Lys Val Gly Lys Ala
         125                 130                 135 aag ggt gat gct ctc ttc aag gct gtt gag gct tac ctt ttg gcc cat    543
Lys Gly Asp Ala Leu Phe Lys Ala Val Glu Ala Tyr Leu Leu Ala His
     140                 145                 150 cct gaa tac aat tgatatcata tcaaccataa tccaatttcc aattcaactt        595
Pro Glu Tyr Asn
155 aatcacactc agatgattat cattatatga taccctatgg tctcaaatta aatgaatcat  655 atatgatatc agtttattaa ggttttttcag gagagttttg ttggtttgca atgttgtcct 715 gtgtgctgaa gttggctttc agtgtaatta ataagtccat gttcattgga ttgaagtatt  775 ttataaactg aagtttgatg aaaaaaaaaa                                   805
```

<210> SEQ ID NO 2
<211> LENGTH: 158
<212> TYPE: PRT
<213> ORGANISM: winged bean

<400> SEQUENCE: 2

```
Met Gly Val Phe Thr Tyr Glu Asp Glu Thr Thr Ser His Val Ala Pro
 1               5                  10                  15

Ala Ile Leu Tyr Lys Ala Ile Val Lys Asp Ala Asp Asn Ile Phe Pro
             20                  25                  30

Lys Ala Val Asp Ser Phe Lys Ser Val Glu Ile Val Glu Gly Asn Gly
         35                  40                  45

Gly Pro Gly Thr Ile Lys Lys Ile Ser Phe Val Glu Asp Gly Glu Ser
     50                  55                  60

Lys Phe Val Leu His Lys Ile Glu Ser Ile Asp Glu Ala Asn Leu Gly
 65                  70                  75                  80

Tyr Ser Tyr Ser Ile Val Gly Gly Ala Ala Leu Pro Ala Thr Val Glu
                 85                  90                  95

Lys Ile Thr Phe Glu Ser Lys Leu Ser Ala Gly Pro Ser Gly Gly Ser
             100                 105                 110
```

```
Val Gly Lys Leu Thr Val Lys Tyr Gln Thr Lys Gly Asp Ala Glu Pro
        115                 120                 125

Asn Glu Glu Leu Lys Val Gly Lys Ala Lys Gly Asp Ala Leu Phe
    130                 135                 140

Lys Ala Val Glu Ala Tyr Leu Leu Ala His Pro Glu Tyr Asn
145                 150                 155
```

```
<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" at position 12 may be A, T, C or G

<400> SEQUENCE: 3
tcrtcytcrt angtraa                                                  17

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: EcoRI
      restriction enzyme site

<400> SEQUENCE: 4
ccgggaattc                                                          10

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" at position 16 may be A, T, C or G

<400> SEQUENCE: 5
ccgggaattc ttyacntakg argayga                                       27

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: adapter
      sequence

<400> SEQUENCE: 6
ccggaattct agagctcgag tttttttttt tttttt                             37

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: adapter
      sequence

<400> SEQUENCE: 7 ccgaattct agagctcgag                                                20
```

LYSINE RICH PROTEIN FROM WINGED BEAN

PRIORITY APPLICATIONS

The present application is a continuation of U.S. patent application Ser. No. 08/804,783, filed Feb. 24, 1997, now abandoned, and U.S. patent application Ser. No. 08/697,309, filed Feb. 22, 1996, now abandoned, which claims priority of the U.S. Provisional Patent Application Ser. Nos. 60/002,918, filed Aug. 29, 1995 and 60/004,266, filed Sep. 25, 1995.

FIELD OF THE INVENTION

The present invention relates to the improvement of seed proteins. More particularly, the invention is directed to a lysine-rich protein isolated from winged bean (WBLRP), its associated nucleic acids and their uses, for example, as expressed in transgenic plants to improve their nutritional qualities.

BACKGROUND OF THE INVENTION

Plants are the primary source of all protein consumed by humans and livestock. In 1990, the world protein supply was 150 million tons, of which 65% was obtained directly from plants and 35% through animal protein production. In comparison to meat, plant protein is much more economical to produce, store, and transport. However, when used as a source of dietary protein for human and monogastric animals, most plant proteins are nutritionally incomplete due to their deficiency in several essential amino acids. In general, cereal (e.g., corn, wheat) proteins are low in lysine (Lys) and tryptophan (Trp), while legume (e.g., soybean) and most vegetable proteins are deficient in the sulfur amino acids, methionine (Met) and cysteine (Cys). See, e.g., Sun and Larkins, in *Transgenic Plants*, vol. 1, King and Wu, Ed. at p. 317 (1992).

To overcome amino acid deficiencies, a mixed diet of cereal and legume, or supplementing plant proteins with meat products or synthetic essential amino acids, typically is employed. U.S. growers annually spend over $120 million and $70 million, respectively, on synthetic Met and Lys to supplement the corn and/or soy protein base of swine and poultry diets. In view of such economic factors, a more direct and cost-efficient means of supplying these amino acids in livestock feed would be highly desirable. See, e.g., Beach et al., in *Biosynthesis and Molecular Requlation of Amino Acids in Plants*, Singh et al., Eds., at p. 229 (1992).

Plant geneticists and breeders have made significant efforts in the past to improve the quality of seed proteins and have developed, e.g., mutant high-lysine corn and barley. However, efforts in breeding legumes containing protein with increased levels of sulfur amino acids have not met with significant success.

Various genetic approaches to the selection or engineering of plant improvements include the selection of cultivars with high levels of desired amino acids, modification of amino acid biosynthesis, and modification of existing proteins. Unfortunately, there often are undesirable traits associated with such modified plants, such as lower yields and greater susceptibility to pests and diseases, and these traits have prevented the agronomic utilization of the plants.

With respect to the selection of high seed protein soybean cultivars, Serretti et al., *Crop Sci.* 34:207–209 (1994) compared the protein and amino acid content of several soybean lines. Similarly, Zarkadas et al., *J. Agric Food Chem.* 41:6161–623 (1993), compared the total protein amino acids and 4-hydroxyproline-rich glycoproteins of a widely-grown soybean cultivar and a high-protein genotype. In one case, however, a high-lysine protein in barley was found to be an inhibitor of chymotrypsin, arguably not a good candidate for nutritional supplementation because chymotrypsin inhibitors can interfere with digestion.

Similarly, U.S. Pat. No. 5,367,110 (1995) to Galili et al. describes transgenic plants that overexpress threonine and lysine. In such plants, a co-transformation process with chimeric genes introduces aspartate kinase activity as well as dihydrodipicolinate synthase activity. This process is intended to enhance the biosynthesis of aspartate-family amino acids, such as lysine, threonine, methionine and isoleucine, in particular the first two amino acids identified.

Alternatively, U.S. Pat. No. 5,258,300 (1993) to Glassman et al. is directed to methods of inducing lysine overproduction in plants by introducing the gene for dihydrodipicolinic acid synthase (DHDPS) which is substantially resistant to feedback inhibition by endogenously-produced free L-lysine. Attached at the 5' terminus of this gene is a sequence encoding a chloroplast transit peptide, which serves to localize the DHDPS in the chloroplasts of transformed cells, where it can act to enhance the biosynthesis of free L-lysine.

Other recent advances in agricultural biotechnology offer other molecular approaches to alter the amino acid composition of seed proteins for improved nutritional quality. The transfer and expression of heterologous genes in plant tissues and plant seeds has been considered promising. It has been demonstrated that a seed protein gene can be transferred and expressed in transgenic plants in a developmentally regulated manner, i.e., the protein product generally is synthesized, transported and properly deposited in the seeds. Moreover, the feasibility of transforming a plant with an essential amino acid-rich protein gene also has been demonstrated.

For example, the research group of one of the present inventors (Dr. Samuel Sun) isolated from Brazil nut a gene encoding a sulfur-rich protein (SRP), having 18% Met and 8% Cys. The SRP gene was subsequently (1989) transferred into tobacco plants to test if the expression of this transgene could enhance the Met content in the transgenic seeds. Results showed that it is feasible to increase the Met content of the transgenic tobacco seeds (by up to 30%) through this molecular approach. See, e.g., Altenbach et al., *Plant Molecular Biology* 13:513–522 (1989). The SRP gene was acquired by Pioneer-Hibred International, Inc., patented by Sun et al., and used for crop protein improvement.

However, what has been needed is method to transform plants in order to achieve overexpression of lysine without the problems and disadvantages associated with prior art approaches. With respect to the expression of heterologous genes, the development of such methods will benefit from a better understanding of how gene transcription is regulated and the structure of seed storage proteins, the development of procedures for transforming and regenerating important seed crops, and the identification and isolation of seed storage protein genes that encode proteins containing high levels of a specific essential amino acid or a combination of these amino acids.

SUMMARY OF THE INVENTION

This invention relates to novel lysine rich proteins isolated from winged bean, and to its variants and modifications.

In still other aspects, the invention provides an isolated nucleic acid molecule encoding a WBLRP and to its allelic variants, labeled or unlabeled, and a nucleic acid sequence that is complementary to, or hybridizes under stringent conditions to, a nucleic acid sequence encoding a WBLRP.

Yet additional aspects of the present invention relates to transformed plant cells and intact plants derived from such cells that express elevated levels of lysine in their seeds.

MODES OF CARRYING OUT THE INVENTION

Figure 1:
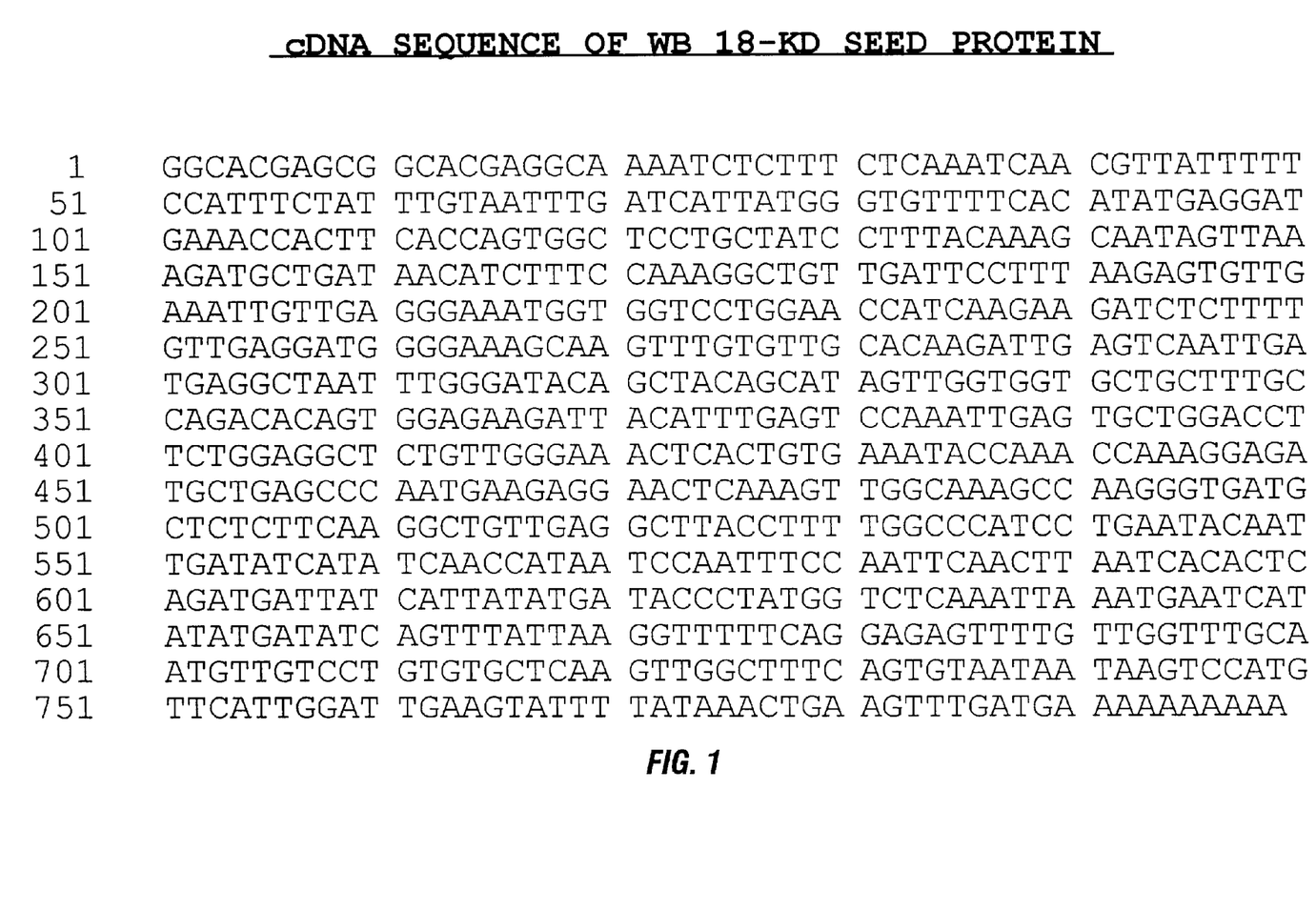
FIG. 1 shows the cDNA sequence (SEQ ID NO:1) of the 18 kD seed protein from winged bean.

We have identified and isolated a Lys-rich protein (WBLRP) from winged bean *Psophocarpus tetragonolobus* and a cDNA encoding the WBLRP was cloned and sequenced (FIG. 1) (SEQ ID NO:1). The deduced amino acid sequence revealed that the 18 kD WBLRP contains 10.83 mol % Lys, representing the most abundant amino acid in this protein (FIG. 2) (SEQ ID NO:2). We have further demonstrated that this gene is expressed only in the developing seeds, and therefore was a good candidate gene for the genetic engineering of seed proteins.

The WBLRP gene can be utilized, through transgenic technology, to enhance the Lys levels of plant proteins. It is particularly valuable in improving the nutritional quality of cereal proteins, including those of corn, wheat, rice and barley, the world's major food crops, which are deficient in Lys. The economic and human nutritional values of this enhancement would be enormous.

As noted above, however, notwithstanding a strong economic motivation to improve plants in this way, prior to our invention, no entirely useful products, without significant detrimental traits, have been reported. The WBLRP of the present invention also can be applied to enhance the Lys content in soybean for use as animal feed, and there are recent studies on the economic implications of this enhancement. For example, the competitive product for Lys-rich soybean meal would be crystalline lysine-HCL, which costs about $1.65/lb and contains 78% lysine. Therefore, a soybean meal contains 1% increased Lys would be worth about $55 more per ton. The estimated total additional value of increasing Lys by 1% in soybean as animal feed is $851 million/year (Economic Implications of Modified Soybean Traits—Special Report 92, Iowa State University and Iowa Soybean Promotion Board & American Soybean Association cooperating, 1990).

In addition to the specific techniques described below, the practice of the present invention will employ conventional techniques of molecular biology, microbiology, recombinant DNA technology, and plant science, all of which are within the skill of the art. Such techniques are explained fully in the literature. See, e.g., Maniatis et al., Molecular Cloning: A Laboratory Manual (1982); DNA Cloning: Volumes I and II (D. N. Glover ed. 1985); Oligonucleotide Synthesis (M. J. Gait ed. 1984); Nucleic Acid Hybridization (B. D. Hames & S. J. Higgins eds. 1985); Transcription and Translation (B. D. Hames & S. J. Higgins, Eds. 1984); Animal Cell Culture (R. I. Freshney ed. 1986); Plant Cell Culture (R. A. Dixon ed. 1985); Propagation of Higher Plants Through Tissue Culture (K. W. Hughes et al. eds. 1978); Cell Culture and Somatic Cell Genetics of Plants (I. K. Vasil ed. 1984); Fraley et al. (1986) CRC Critical Reviews in Plant Sciences 4:1 (hereinafter Plant Sciences); Biotechnology in Agricultural Chemistry: ACS Symposium Series 334 (LeBaron et al. eds. 1987); and Genetic Engineering, Vol. 6 (Rigby ed., 1987).

In describing the present invention, the following terminology will be used in accordance with the definitions below.

A "replicon" is any genetic element (e.g., plasmid, cosmid, chromosome, virus, etc.) that behaves as an autonomous unit of DNA replication in vivo; i.e., capable of replication under its own control within a cell.

A "vector" is a replicon, such as a plasmid, cosmid, or bacteriophage, to which another DNA segment may be attached so as to bring about replication of the attached segment, or to allow its introduction into a cellular host.

A "DNA molecule" is a species of nucleic acid, as defined below, and refers to the polymeric form of deoxyribonucleotides (adenine, guanine, thymine, or cytosine) in either single- or double-stranded form. The double-stranded form may, of course, be implied by the context of the molecule's environment (e.g., a chromosome). When in the double-stranded form, the molecule will usually be in its normal, double-stranded helix. The term "DNA molecule" is not limited to any particular tertiary form of DNA. Thus, the term includes double-stranded DNA found, inter alia, in linear DNA molecules, viruses, plasmids, and chromosomes. When discussing the structure of particular double-stranded DNA molecules, sequences may be described herein according to the normal conventions.

A DNA "coding sequence" is a DNA sequence which is transcribed and translated into a polypeptide in vivo when placed under the control of appropriate regulatory sequences. The boundaries of the coding sequence are determined by the start codon at the 5' terminus and a translation stop codon at the 3' terminus. Examples of coding sequences include cDNA reverse transcribed from eukaryotic mRNA, genomic DNA sequences from eukaryotic cells, and synthetic DNA sequences.

A cell which has been "transformed" by an exogenous DNA sequence is a cell into which the exogenous DNA has been introduced. The exogenous DNA may be integrated (covalently linked) to chromosomal DNA making up the genome of the cell, or it may remain extrachromosomal. "Stably" integrated DNA sequences are those which are inherited through chromosome replication by daughter cells or organisms (accounting for loss by Mendelian segregation). This stability is exhibited by the ability to establish cell lines or clones comprised of a population containing the exogenous DNA.

A "clone" or "cell line" is a population of cells descended from a single cell or common ancestor by mitosis and is capable of stable growth in vitro for many generations.

A composition of a first type of matter (e.g., a DNA molecule containing a coding region) is "substantially free" of a second type of matter (e.g., DNA molecules which do not contain a coding region) if the composition is comprised of less than about 10% (weight/weight) of the second type of matter relative to the sum of the first and second types of matter. Preferably, the composition contains less than about 5% of the second type of matter, most preferably less than about 1%.

Two sequences, such as nucleic acid sequences or amino acid sequences, are "substantially homologous" when the sequences are a minimum of about 80% homologous over a selected region, preferably at least about 90% homologous, and more preferably at least about 95% homologous. Identity or homology with respect to a common sequence is defined herein as the percentage of nucleic acids or amino acid residues in the candidate sequence that are identical with the WBLRP DNA or protein disclosed herein, after aligning the sequences and introducing gaps, if necessary, to achieve the maximum percent homology, and not considering any conservative substitutions as part of the sequence identity. None of N-terminal, C-terminal or internal extensions, deletions, or insertions into the WBLRP sequence shall be construed as affecting homology.

Figure 2:
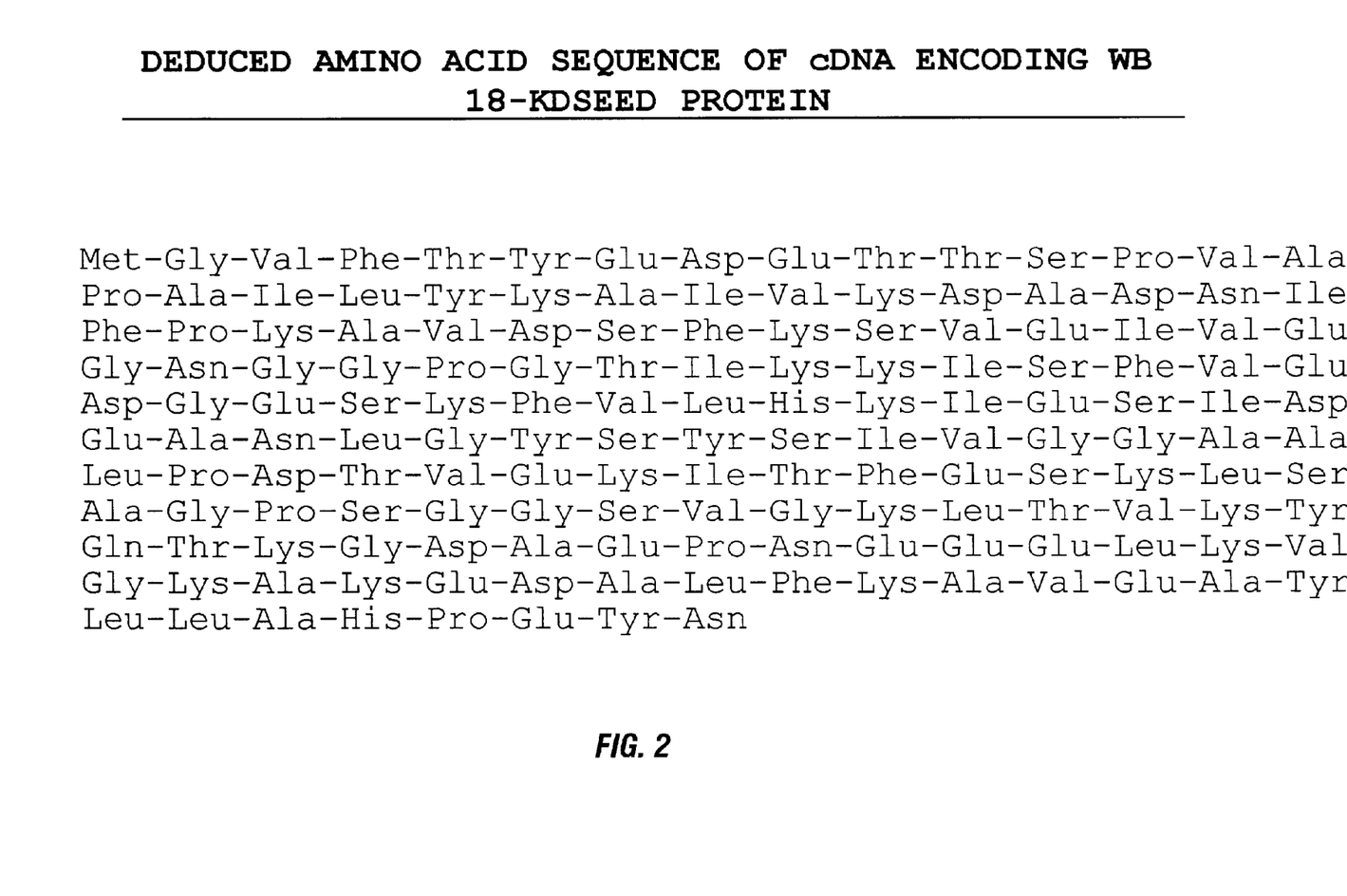
FIG. 2 show the deduced amino acid sequence (SEQ ID NO:2) of the 18 kD seed protein from winged bean.
Figure 3A:
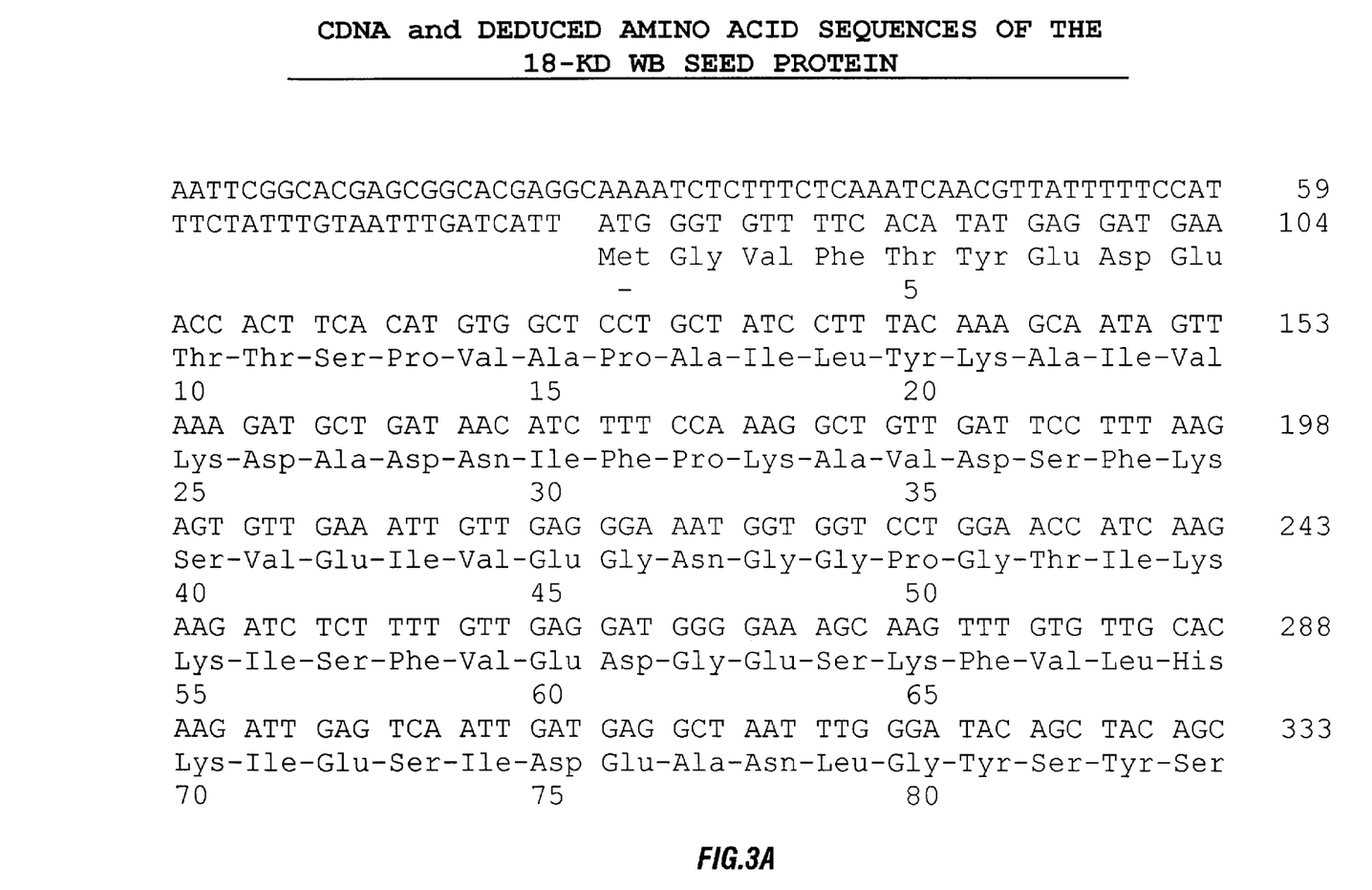
FIGS. 3A and 3B show the cDNA (SEQ ID NO:1) and deduced amino acid (SEQ ID NO:2) sequences of the 18-KD WB seed protein.
Figure 3B:
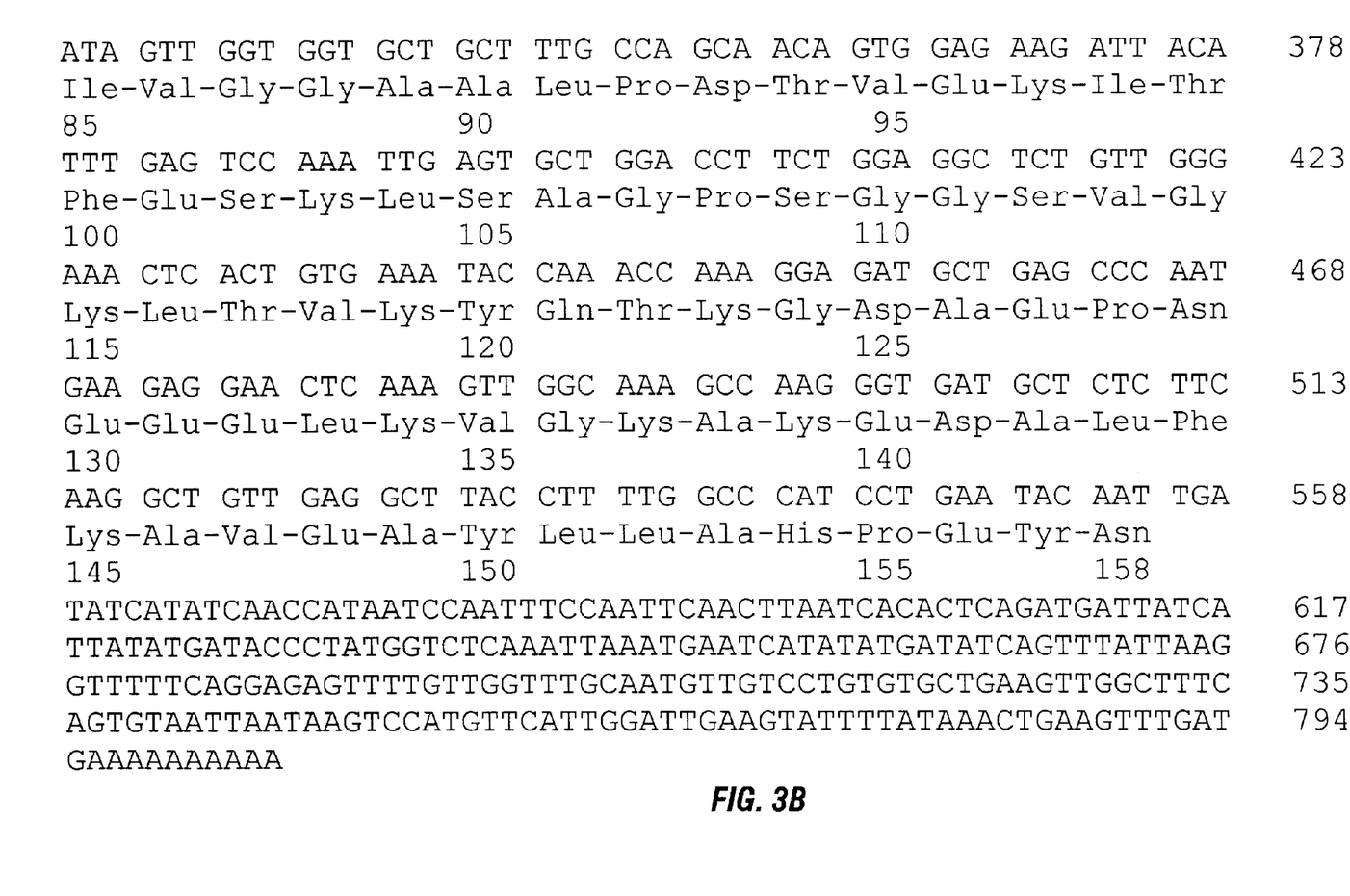

WBLRP "nucleic acid" is defined as RNA or DNA that encodes a WBLRP, or is complementary to nucleic acid sequence encoding a WBLRP, or hybridizes to such nucleic acid and remains stably bound to it under stringent conditions, or encodes a polypeptide sharing at least 80% sequence identity, preferably at least 90%, and more preferably at least 95%, with the translated amino acid sequences shown in FIG. 2. Specifically contemplated are genomic DNA, cDNA, mRNA and antisense molecules, as well as nucleic acids based on alternative backbone or including alternative bases whether derived from natural sources or synthesized. Such hybridizing or complementary nucleic acid, however, is defined further as being novel and unobvious over any prior art nucleic acid including that which encodes, hybridizes under stringent conditions, or is complementary to nucleic acid encoding a WBLRP or a pathogenesis-related protein as described below.

"Stringent conditions" are those that (1) employ low ionic strength and high temperature for washing, for example, 0.015 M NaCl/0.0015 M sodium titrate/0.1% NaDodSO4 at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075 M sodium citrate), 50 mM sodium phosphate (pH 6.8), 0.1% sodium pyrophosphate, 5× Denhardt's solution, sonicated salmon sperm DNA (50 mu g/ml), 0.1% SDS, and 10% dextran sulfate at 42° C., with washes at 42° C. in 0.2×SSC and 0.1% SDS.

"Isolated" nucleic acid will be nucleic acid that is identified and substantially free from other nucleic acid molecules, as defined above in the case of DNA. The nucleic acid may be labeled for probe purposes, using any label known and described in the art as useful in connection with diagnostic assays.

Of particular interest is a WBLRP nucleic acid that encodes a full-length molecule, including but not necessarily the native signal sequence thereof. Nucleic acid encoding full-length protein may be obtained as described above by screening selected cDNA or genomic libraries using the deduced amino acid sequence disclosed herein for the first time, and, if necessary, using conventional primer extension procedures to secure DNA that is complete at its 5' coding end. Such a clone is readily identified by the presence of a start codon in a reading frame with the original sequence.

DNA encoding an amino acid sequence variant of a WBLRP is prepared as described below or by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of a WBLRP.

Techniques for isolating and manipulating nucleic acids are disclosed for example by the following documents: U.S. Pat. No. 5,030,576, U.S. Pat. No. 5,030,576 and International Patent Publications WO94/11504 and WO93/03162. See, also, Sambrook, J. et al., *Molecular Cloning: A Laboratory Manual*, 2nd Edition, Cold Spring Harbor Press, Cold Spring Harbor, N.Y., 1989, and Ausubel, F. M. et al. *Current Protocols in Molecular Biology*, Vol. 2, Wiley-Interscience, New York, 1987.

The claimed WBLRP protein and analog molecules that are the subject of this invention include molecules having the WBLRP amino acid sequence; fragments thereof having a consecutive sequence of at least 10, 15, 20, 25, 30 or 40 amino acid residues from a common WBLRP sequence; amino acid sequence variants of a common WBLRP sequence wherein an amino acid residue has been inserted N- or C-terminal to, or within, the WBLRP sequence or its fragments as defined above; amino acid sequence variants of the common WBLRP sequence or its fragment as defined above which have been substituted by another residue. WBLRP polypeptides include those containing predetermined mutations by, e.g., homologous recombination, site-directed or PCR mutagenesis, and WBLRP polypeptides of other plant animal species, and alleles or other naturally occurring variants of the WBLRP; derivatives of the commonly known WBLRP or its fragments wherein the WBLRP or its fragments have been covalently modified by substitution, chemical, enzymatic, or other appropriate means with a moiety other than a naturally occurring amino acid (for example a detectable moiety such as an enzyme or radioisotope); glycosylation variants of WBLRP (insertion of a glycosylation site or deletion of any glycosylation site by deletion, insertion or substitution of appropriate amino acid); and soluble forms of WBLRP.

The novel nucleic acids and their associated proteins and peptides of the present invention are preferably those which share the enhanced lysine levels of WBLRP and are capable of expression in transformed plants, but such nucleic acids and protein fragments and variants exclude any WBLRP polypeptide heretofore made public, including any known protein or polypeptide of any plant species, which is otherwise anticipatory under 35 U.S.C. §102 as well as polypeptides obvious over such known protein or polypeptides under 35 U.S.C. §103.

In accordance with the present invention, a nucleic acid molecule is provided which contains, e.g., a DNA coding region that encodes a WBLRP seed storage protein of *S. tetragonolobus*. Related DNA molecules can encode either a genomic or cDNA sequence, and either a complete presequence, or a mature sequence. DNA molecules according to the present invention can be comprised of a coding region which is entirely homologous to native DNA; e.g., cDNA or genomic DNA. Alternatively, the coding region can be partially or completely synthetic in nature; e.g., comprised of codons different than that found in the native plant, yet encoding substantially the same protein. This may be particularly preferred when it is intended to express the coding region in a heterologous host, thereby allowing for the selection of host-preferred codons. See, e.g., U.S. Pat. No. 4,356,270; and EPO Pub. No. 46,039.

In a preferred embodiment of the present invention, the DNA sequences encoding WBLRP will be "flanked by DNA sequences heterologous" to the WBLRP coding sequences. This means that the coding sequences flanked at both the 5' and 3' ends by DNA which is not found in the comparable flanking positions in the *S. tetragonolobus* wild-type genome. Examples of DNA constructs falling within this definition include-plasmids carrying WBLRP-encoding sequences, linear DNA sequences containing non-*S. tetragonolobus* DNA in the 5' and 3' positions, or a *S. tetragonolobus* chromosome transformed with a WBLRP-encoding sequence that integrates at a position other than the location of the wild-type gene. Particularly preferred flanking, heterologous sequences are those elements which make up the expression cassettes described below.

DNA molecules encoding WBLRP can be prepared synthetically by known methods of oligonucleotide synthesis. Synthetic coding sequences can be prepared from overlapping oligonucleotides whose sequence contain codons for the amino acid sequence of the storage protein. Such oligonucleotides are prepared by standard methods and assembled into a complete coding sequence. See, e.g., Edge (1981) Nature 291:756; Nambiar et al. (1984) Science 323:1299; Jay et al. (1984) J. Biol. Chem. 259:6311; oligonucleotide Synthesis (above).

WBLRP coding sequences can also be isolated employing methods of screening cDNA or genomic libraries. While short probes can be prepared from the nucleic acid sequences disclosed herein, it is preferred to employ the entire coding sequences disclosed herein as a probe when screening libraries for other variants. Due to the homology between the variants, isolation of additional DNA sequences encoding different isoproteins is within the skill of the art by employing the nucleic acid sequences disclosed herein as probes. See, e.g., Molecular Cloning: A Laboratory Manual (above); DNA Cloning: Vol. I & II (above); Nucleic Acid Hybridization (above).

The synthesis or isolation of DNA molecules containing the described coding sequences permits those of skill in the art to prepare compositions of DNA molecules encoding WBLRP substantially free of DNA molecules which do not encode the lysiner-rich protein. The compositions of DNA molecules containing coding sequence according to the present invention can be comprised of linear coding sequences, or coding sequences in cloning vectors. Numerous cloning vectors are known to those skilled in the art, and the selection of an appropriate cloning vector is a matter of choice. Examples of recombinant DNA vectors for cloning in the host cells which they transform include bacteriophage lambda (*E. coli*), pBR322 (*E. coli*), pACYC177 (*E. coli*), pKT230 (gram-negative bacteria), pGV1106 (gram-negative bacteria), pLAF 1 (gram-negative bacteria), pME290 (non-*E. coli* gram-negative bacteria), pHV14 (*E. coli* and *Bacillus subtilis*), pBD9 (bacillus), pIJ61 (Streptomyces), pUC6 (Streptomyces), actinophage phi C31 (Streptomyces), YIp5 (yeast), YCp19 (yeast), and bovine papilloma virus (mammalian cells). See, generally, DNA Cloning: Volumes I & II (above); and Molecular Cloning: A Laboratory Manual (above).

In accordance with the present invention, DNA constructs are provided in which the above-described coding sequences are placed under the control of transcription regulatory sequences so that the WBLRP storage protein is expressed in a host cell. Such DNA constructs, referred to as "expression cassettes", are comprised of the storage protein coding sequence under the control of regulatory sequences, such as a promoter, ribosome binding site (for bacterial expression) and a transcription termination sequence or polyadenylation signal. Other regulatory sequences include operators, enhancers, and the like. The cassette is usually flanked by convenient restriction sites. The selection of the appropriate regulatory sequence and coding sequence, as well as their assembly for expression in a particular host, is within the skill of the art.

It is usually desirable to include within the expression cassette a selectable marker. A "selectable marker" gene encodes a "selectable phenotype"; i.e., a phenotype of a cell or organism which allows for the identification or selection of cells expressing the selectable marker gene. Well-known marker genes are known in the art, including, but not limited to, the gene for chloramphenicol acetyltransferase (CAT), neomycin phosphotransferase (neo<5>), neomycin phosphotransferase II (npt-II), nopaline synthase (NOS), hygromycin phosphotransferase, the glyphosate resistance gene (EPSP), dihydrofolate reductase (mtx<R>), hypoxanthine phosphoribosyltransferase (hpt), and thymidine kinase (tk). Cells transformed with sequences encoding these proteins are able to survive on media which would otherwise be toxic to the cell. Other types of markers, such as beta-galactosidase (lacZ) cause cells transformed therewith to change color under certain conditions, thus allowing for visual selection. The presence of the selectable marker in the expression cassette allows for the determination of whether a particular cell has been transformed stably by the expression cassette. Selectable markers can be included which function in the ultimate host which will express the storage protein, as well as additional markers which will function in intermediate hosts in which the construction of the expression cassette occurs.

The expression cassette is constructed so that the coding sequence is located within the cassette with the appropriate control sequences, the positioning and orientation of the coding sequence with respect to the control sequences being such that the coding sequence can be transcribed under the control of the regulatory sequences (i.e., by RNA polymerase which attached to the DNA molecule at the control sequences) in a host cell transformed by the expression cassette.

It is possible to assemble the expression cassette prior to inserting it into a cloning vector as described above. Alternatively, an expression cassette can be constructed by cloning the coding sequence directly into an expression vector already containing the appropriate regulatory sequences and a restriction site downstream from the promoter.

Construction of expression vectors or expression cassettes for use in transforming microbial hosts (e.g., bacteria or yeast) may be desired to produce single-cell protein by fermentation to supplement the nutritive value of other protein sources. A number of prokaryotic expression vectors are known in the art which could be adapted for this purpose See, e.g., U.S. Pat. Nos. 4,440,859; 4,436,815; 4,431,740; 4,431,739; 4,428,941; 4,425,437; 4,418,149; 4,411,994; 4,366,246; and 4,342,832. See also British Patent Nos. 2,121,054; 2,008,123; 2,007,675; and European Patent Pub. No. 103,395. Yeast expression vectors are also known in the art. See, e.g., U.S. Pat. Nos. 4,446,235; 4,443,539; 4,430,428; 4,546,082. See also European Patent Pub. Nos. 103,409; 100,561; and 96,491.

A preferred class of heterologous hosts for the expression cassettes containing coding regions for WBLRP are eukaryotic hosts, particularly the cells of higher plants (dicots, monocots). Particularly preferred among the higher plants are those of agronomic value having edible parts, such as leguminous plants, including, but not limited to, *Glycine max* (soybean), *Medicaqo sativa* (alfalfa), *Psophocarpus tetragonolobus* (winged bean), and *Vigna aconitifolia* (moth bean). Other bean cultivars, such as *P. vulgaris*, can be useful hosts. Crops in general, such as maize, may also be useful hosts.

Expression cassettes intended for use in higher plants will employ regulatory sequences functional in such plants. For example, promoters can be selected from the group consisting of plant promoters, plant virus promoters, and T-DNA promoters (from both Ti and Ri plasmids). Specific T-DNA promoters known in the art include the nopaline synthase (NOS) promoter, and the octopine synthase (OCS) promoter. These promoters are constitutive promoters. See, e.g., Plant Sciences (above). Examples of plant virus promoters include the 19S and 35S transcript promoters from cauliflower mosaic virus (CaMV). See, e.g., Id.; Koziel et al. (1984) J. Mol. Appl. Genet. 2:549. Numerous plant promoters have been shown to work in heterologous systems, including, but not limited to, the pea small subunit RUBP carboxylase (pSS) promoter, Morelli et al. (1985) Nature (London) 315:200; Broglie et al. (1984) Science 224:838; Herrera-Estrella et al. (1984) Nature (London) 310:115; Coruzzi et al. (1984) EMBO J.3:1671; the soybean small subunit RUBP carboxylase (SbSS) promoter, Facciotti et al. (1985) Bio/Technology 3:241; the maize zein promoter, Matzke et al. (1984) EMBO J. 3: 1525; the wheat chlorophyll a/b binding protein promoter, Lampa et al. (1985) Mol. Cell. Biol. 5:1370–1378; soybean 7S alpha, conglycinin promoter, Beachy et al. (1985) EMBO J. 4:3047; the soybean glycinin G2 promoter; soybean heat-shock promoter, EPO Publication No. 159,884; and the french bean phaseolin promoter, Sengupta-Gopalan et al. (1985) Proc. Natl. Acad. Sci. USA 82:3320; Murai et al. (1984) Science 222:476. Depending upon the application, it may be desirable to select from among the available promoters those which are tissue specific (e.g., seed, leave, etc.) and/or regulated (e.g., light-induced, temperature or heat-induced, developmentally regulated, etc.).

Particularly preferred promoters are those which allow for expression of WBLRP in seeds of heterologous plants. Examples of such promoters include, but are not limited to, the phaseolin promoter and the soybean 7S alpha' conglycinin promoter. Expression cassettes intended for seed-specific expression can employ either heterologous promoters such as these, or the homologous promoter. In like manner, expression cassettes can employ heterologous signal peptides in a coding sequence, particularly those associated with the heterologous promoter, or WBLRP's own signal peptide.

Various methods of transforming cells of higher plants with expression cassettes according to the present invention are available to those skilled in the art. See generally, Lichtenstein et al. in Genetic Engineering: Vol. 6, pp. 104–182 (Rigby ed. 1987). Among the most popular of transformation methods are those based on transformation vectors constructed of T-DNA from Ti or Ri plasmids. It is particularly preferred to use binary T-DNA vectors. See, e.g., Plant Sciences, above. T-DNA based vectors have been shown to transform dicots and monocots, including, but not limited to, legumes (e.g., soybean, peas, and alfalfa), cotton, rape, tomato, Liliaceae (e.g., asparagus), Amaryllidaceae, etc. See, e.g., Plant Siences, above, and references sited therein; Pacciotti et al. (1985) Bio/Technology 3:241; Byrne et al. (1987) Plant Cell, Tissue and Organ Culture 8:3; Sukhapinda et al. (1987) Plants Mol. Bio. 8:209–216; Lorz et al. (1984) Proceedings of EEC-Symp.: In Vitro Techniques-Propagation and Long-Term Storage; Lorz et al. (1985) Mol. Gen. Genet. 199:178; and Potrykus et al. (1985) Mol. Gen. Genet. 199:183.

Other transformation methods are available to those skilled in the art. Viral transformation vectors are known, such as those based on CaMV. See, e.g., Brisson et al. (1984) Nature (London) 310:511; Gronenborn et al.(1981) Nature (London) 294:773. Transposons can also be used to transform plants, particularly monocots. Maize transposons include, for example, Ac and Ds transposons, as well as the Mul transposon. See, e.g., Plant Sciences, above, at p. 28.

In the absence of a suitable transformation vector for desired higher plant host, such cells can be transformed by the direct uptake of DNA including expression cassettes of the present invention. The uptake of foreign DNA in plant cells using various chemical agents is known. See, e.g., Davey et al. (1980) Plant Sci. Lett. 18:307; Draper et al. (1982) Plant Cell Physiol. 23:1; Krens et al. (1982) Nature (London) 296:72; Hain et al. (1985) Mol. Gen. Genet. 199:161; Hooykaas-van Slogteren et al. (1984) Nature (London) 311:763; Hernalsteens et al. (1985) EMBO J. 3:3039. Higher plant protoplasts have also been transformed by techniques of electroporation. See, e.g., Fromm et al (1986) Nature (London) 319:791; Fromm et al. (1985) Proc. Natl. Acad. Sci. USA 82:5824; Potter et al. (1984) Proc. Natl. Acad. Sci. USA 81:7161. Plant cells may also be transformed with foreign DNA by micro-injection using known techniques, or by high-velocity metal particles coated with RNA or DNA. See, e.g., Kline et al. (1987) Nature (London) 327:70.

Once transformed plant cells have been produced, it is usually desirable to grow transformed cells into callous tissue or a cell line in suspension. Techniques for regenerating callous and for producing cell lines are known in the art. See, e.g., Plant Cell Culture, above; Propagation of Higher Plants Through Tissue Culture, above. Transformed cells can also be induced to undergo organogenesis. Thus, transformed cells can be maintained as undifferentiated tissues, or in organ culture. These plant cell cultures or organ cultures can be used, therefore, to produce WBLRP. See, e.g., Flores in Biotechnology and Agricultural Chemistry; ASC Symposium Series 334, p.66 (LeBaron et al. eds., 1987).

Another important application of the present invention is the production of plants transformed with the coding sequences for WBLRP. Techniques for regenerating plants from tissue culture, such as transformed protoplasts or callous cell lines, are known in the art. See, e.g., Bingham et al. (1975) Crop Sci. 15:719–721; Kao et al. (1980) Z. Pflanzenphysiol Bd. 96:135–141; Reisch et al. (1980) Plant Sci. Lett. 20:71–77; U.S. Pat. No. 4,548,901; Wright et al. (1987) Plant Cell Rpts. 6:83; Christianson et al. (1983) Science 222:632; Hammatt et al. (1987) Plant Science 48:129; Ghazi et al. (1986) Plant Cell Rpts. 5:452; Barwale et al. 1986) Planta 167:473; Newell et al. (1985) Plant Cell Tissue Organ Culture 4:145; Phillips et al. (1981) Plant Cell Tissue Organ Culture 1:123; Eapen et al. (1986) Theor. Appl. Genet. 72:384; Krishnamurthy et al. (1984) Plant Cell Rpts. 3:30; Shekhawat et al. (1983) Plant Sci. Lett. 32:43; Wilson et al. (1985) Plant Sci. 41:61; Venstesnaran et al. (1985) In Vitro 21(3, II): 36A. The selection of an appropriate method is within the skill of the art.

Set forth below are specific examples of the present invention which are intended for illustrative purposes only. These examples are not intended to limit the present invention in any manner. The references cited in this application are incorporated by reference in their entireties.

EXAMPLE 1

A. Identification of Seeds Rich in Lysine—The Winged Bean

1. Seeds from 10 plant species of six families, as listed below, were selected for total protein extraction and analysis.

Corylus spp. (hazel nut)

Brassica spp. Chinese green mustard)

*Carya cathayensis* (mountain walnut)

*Juglans regia* (English walnut)

*Vigna radiata* (mung bean), 3 varieties

*Psophocazpus tetraqonolobus* (winged bean)

*Sesame indicum* (sesame)

*Pinus tabulaeformis* (Chinese pine)

2. The amino acid composition of the 10 protein samples was determined by an automated amino acid analyzer.

3. From the amino acid profiles of the 10 protein samples, winged bean was identified as having the highest lysine content, 7.9% (g/100 g).

B. Identification of Winged Bean Polypeptide(s) Rich in Lysine—the 18-KD Protein 1. The polypeptides in the total seed protein extract of winged bean were separated by sodium dodecyl sulfate-polyacrylamide gel electrophoresis (SDS-PAGE) into different size species.

2. Twenty one individual polypeptides differing in molecular weight were excised and eluted from the SDS-PAGE gel and their amino acid compositions determined.

3. From the amino acid profiles of the 21 polypeptide species, an 18-KD polypeptide was identified to contain the highest amount of lysine, 10.17% (mg/100 mg), and named winged bean lysine-rich protein (WBLRP).

C. Determination of the N-Terminal Amino Acid Sequence of WBLRP

1. The N-terminal amino acid sequence of WBLRP was determined. The sequence of the first 9 amino acids as determined and confirmed is as shown below (amino acids 1–9 of SEQ ID NO:2):

NH₂Met—Gly-Val-Phe-Thr-Tyr-Glu-Asp-Glu—COOH

EXAMPLE 2

Cloning the cDNA Encoding the Winged Bean 18-kD LRP

The cloning the cDNA encoding the WBLRP was achieved with the following approach: verify the presence of the mRNA encoding the WBLRP in the developing winged bean seeds; amplify and clone the mRNA encoding the WBLRP by PCR technique; construct a cDNA library for the developing winged bean seeds; screen the cDNA library using the PCR generated WBLRP cDNA as a probe; and sequence and further characterize the cDNAs encoding the WBLRP.

A. Identification of mRNA Encoding the 18-KD WBLRP in Developing Winged Bean Seeds 1. On the basis of the N-terminal sequence obtained for the (I.C2), a 17-mer oligonucleotide mixed probe, WB-NT1, with a degeneracy of 1/64 and complementary to the mRNA, was synthesized:

```
17-mer WB-NT1 (SEQ ID NO:3):5' - T C A T C T T C A T A A G T A A A - 3'
                                     G     C     G     G     G
                                                       T
                                                       C Corresponding              C - Glu - Asp - Glu - Tyr - Thr - Phe -
WBLRP N-                        9     8     7     6     5     4
terminal sequence: (amino acids 4–9 of SEQ ID NO:2)
```

2. Total RNA was extracted from maturing winged bean cotyledons (Hall, et al., 1978. Proc. Natl. Acad. Sci. USA 75:3196–3200) and separated by formaldehyde gel electrophoresis.

3. The winged bean RNA was transferred from the gel to nitrocellulose filter (northern blotting) and hybridized to the ³²P labeled 17-mer WB-NT1 probe.

4. A mRNA species with molecular size of 700 NT was identified for the WBLRP, indicating that the RNA prepared from the developing winged bean cotyledons contains the mRNA for the WBLRP, and thus justifying the use of this RNA for cloning the LRP gene.

B. Amplification of the WBLRP nMRA and Cloning the Amplified Product

1. To amplify and clone the cDNAs encoding the WBLRP using polymerase chain reaction (PCR) technique, three oligonucleotide primers were synthesized, a WBLRP gene specific primer, WB-NT2 or P2, and two universal primers for priming poly(A) RNA, Oligo(dT)-adapter or P1, and Adapter or P3.

This 26-mer oligonucleotide primer consists of a mixture of 17 nucleotides (degeneracy, 1/64) that are synthesized based on the N-terminal amino acid sequence of WBLRP, NH₂-Phe-thr-Tyr-Glu-Asp-Glu (the 4th to 9th amino acids) and a 10-nucleotide region contains an EcoRI restriction enzyme site (SEQ ID NO:4) (CCGGGAATTC) to facilitate the cloning of the PCR products. P2 is the 5' PCR primer for amplifying the WBLRP mRNA.

Primer Oligo(dT)-Adaptor or P1a:

This 37-mer primer consists of 17 (dT) nucleotides for priming the poly (A) tail of any mRNA and a 20-nucleotide region that contains multiple restriction sites including EcoRI to facilitate the cloning of PCR products. P1 is the 3' primer for transcribing the mRNA (to produce the first strand cDNA).

Primer Adapter or P3:

This 20-mer primer contains multiple restriction sites including EcoRI. It is identical to the adapter sequence of P1 and is used to prime the 2nd strand cDNA for continuous synthesis of the first strand cDNA.

2. The mRNA encoding the WBLRP was amplified by the PCR technique, RACE (Rapid Amplification of cDNA Ends) (Frohman, et. al., 1993. Methods in Enzymology 218:340–356). In this technique, all the mRNAs of the developing winged bean cotyledons were first reverse transcribed to generate a mixture of complementary DNAs (first strand cDNAs) using the P1 primer (Oligo(dT)—adapter) and reverse transcriptase. The first strand WBLRP cDNA in the pool of mixed cDNAs was then selectively transcribed (into 2nd strand cDNA) using the P2 (WB-NT2) gene specific primer by Taq polymerase Primer P3 (Adapter) was then used to multiply the first strand LRP cDNA. A total of 30 cycle of amplification was carried out.

3. After amplification, the PCR products were separated by (2% low melting) agarose gel electrophoresis. Two major DNA bands, 700bp and 400bp, were observed. The 700-bp and 400-bp DNA fragments were excised and purified from the gel (by Promega's Wizard™ PCR Preps-DNA Purification System). After digestion with ECoRI and purification through Millipore's Ultrafree-MC column, the 700-bp and 400-bp EcoRI DNA fragments were inserted into the pBluescript KS+ vector stratagene) and transformed into E. coli DH5α competent cells.

4. Colonies with the vector and insert DNA were identified. The nucleotide sequences of the insert DNAs were determined by the dideoxy sequencing procedure (Hanger et al., 1977. Proc. Natl. Acad. Sci., USA 74:5463–5467) using the T3 and T7 primers and the Sequence of United States Biochemical.

5. Comparison of the cloned nucleotide sequences with the known N-terminal WBBRP sequence revealed that the 700-bp PCR cDNA clones encode the WBLRP but not the 400-bp DNA. The entire sequence of 742 bp (excluding the poly A tail) of clone WB7-28 was determined. The N-terminal sequence of the deduced protein sequence matches with that of the 18-KD WBLRP. The deduced amino acid sequence contains 155 residues (missing two because the primer starts from the 3rd amino acid), of which 17 are lysine. This cDNA thus encodes a protein rich in Lys (10.83 mol % Lys).

C. Cloning the CDNA for WBLRP

The strategy of cloning a cDNA encoding the WBLRP is to first construct a cDNA library for the developing winged bean cotyledons and then screen the library, using the PCR-cloned WBLRP cDNA as a probe, to identify a full-length cDNA encoding the WBLRP.

1. Poly(A) RNA was isolated from the total winged bean RNA by the PolyATract mRNA Isolation System of Promega.

2. A cDNA library was constructed by the ZAP cDNA Synthesis and Cloning System of Stratagene using 5 μg of winged bean poly(A) RNA. A total of 9×10⁶ recombinant clones was obtained for the primary cDNA library and 1.8×10⁹ recombinant clones for the amplified library.

3. The PCR-cloned WBLRP cDNA, WB7-28, was labeled with $^{32}$p by the method of random priming and used as a probe to screen the winged bean cDNA library. Positive clones were identified and their sequences determined.

4. The complete nucleotide sequence of cDNA clone WB-3 was determined. The total length of WB-3 is 782 bp excluding the poly A tail. It contains a 5' untranslated region of 68 nucleotides, a coding region of 474 nucleotides, and a 3' untranslated region of 240 nucleotides. The coding region encodes a protein of 157 amino acids with a molecular weight of 19,494 daltons (thus 1,494 daltons more than the 18-KD estimated by SDS-PAGE). There are 17 residues of Lys, representing 10.83 mol % of the total amino acids.

EXAMPLE 3

Further Characterization of the WBLRP Gene

A. Sequence Homology with the Pathogenesis-Related Proteins

A search of the sequence data in the GenBank revealed that the WBLRP share high sequence homology (50–87%) with those of the many pathogenesis-related (PR) proteins. PR proteins accumulate as a part of a defense response system in many plants exposed to viroids, viruses, fungi, bacteria and other stresses (Linthorst, H. J. M., 1991. Critical Rev. Plant Sci., 10:123–150; Fristensky, B. et al., 1988. Plant Mol. Biol. 11:713–715; and Crowell, D. N. et al., 1992. Plant Mol. Biol. 18:459–466). Upon calculating the lysine content of the available sequences of PR proteins, we found that these proteins, like WBLRP, are rich in lysine. However, in the literature on PR proteins, there was no noticeable attention paid to the high lysine content of these proteins, nor any recognition of the potential use of these proteins for nutritional quality improvement. This may be due to the scientists working in the PR protein area center their interest only in the pathogenicity aspects of these proteins, or the involvement of the PR proteins in plant diseases renders these proteins unattractive for potential use in plant nutrition improvement. Thus, the literature might reveal the utility of the PR proteins for disease resistance and not for plant nutrition improvements.

B. WBLRP: Special Biological Characteristics Favoring its use for Plant Nutrition Improvement We have carried out further experiments to investigate the molecular biology of the WBLRP. Unlike most PR proteins that are synthesized in response to pathogen infection and wounding, chemical and other stresses, we found that the WBLRP is a relatively abundant protein (2% as total protein) in the seeds of winged bean. Northern hybridization experiments revealed that the expression of the WBLRP gene is organ specific, i.e. the WBLRP gene only expressed in the seed but not in the leaf, stem, root, or flower. The expression of the WBLRP gene is also developmentally regulated. Specifically, the expression of the WBLRP in the developing seeds starts 20 days after flowering (DAF), peaks at 35 DAF, and declines 45 DAF. Thus the WBLRP gene is under tight control for spatial and temporal expression in the normally developing winged bean seeds; in this respect, its expression is not related to pathogen activity or wounding. The synthesis and accumulation of the lysine-rich protein in abundance in the seeds makes the WBLRP gene a suitable target for plant (especially seed) nutrition improvement.

EXAMPLE 4

The Construction of Transgenic Plants

Plants transformed with a vector comprising the WBLRP protein are prepared as follows. To illustrate, transformation of rapeseed for enhanced lysine content will be described.

A chimeric gene containing the WBLRP coding sequence (cDNA) under the regulation of the French bean seed-specific phaseolin promoter and terminator sequences will be constructed. This chimeric gene is then inserted into the Agrobacterium transformation vector, pBI121. The vector harboring the WBLRP chimeric gene will then be transferred into A. tumefaciens LBA4404, and used to transform the rapeseed explants.

The transformation and regeneration of several commercial cultivars of rapeseed plants are well documented and established. To summarize, there are three major procedures for rapeseed transformation: 1. stem segments as explants via *A. rhizogenes* (Guerche et al. *Mol. Gen. Genet.* 202:382–386, 1987) or *A. tumefaciens* (Pua et al. *Bio/Tech.* 5:815–817, 1987); 2. Hypocotyls as explants via *A. tumefaciens* (De Block et al., *Plant Physiol.* 91:694–701, 1989) or *A. rhizogenes*, Damgaard & Rasmussen, *Plant Mol. Biol.* 17:1–8, 1991); and 3. Protoplasts as starting materials via electroporation (Guerche et al., *Plant Sci.* 52:111–116, 1987). Using these procedures, transgenic rapeseed plants with normal phenotype and full fertility can be generated in about four months.

The procedure using *A. tumefaciens* to transform the hypocotyl segments of rapeseed will be followed. In the present example, the *A. tumefaciens* LBA4404 carrying the WBLRP chimeric gene will be used to transform the rapeseed cultivar Westar, a spring cultivar, and the transgenic plants will be recovered, as detailed by Altenbach et al., *Plant Mol. Biol.* 18:235–245.

The integration of the WBLRP chimeric gene into the rapeseed genome will be detected by Southern blot hybridization using the WBLRP cDNA as a probe. The expression of the transgene in the transgenic seeds will be determined by: 1) Northern blot hybridization, using WBLRP cDNA as a probe, for the WBLRP transcripts (mRNA), and 2) Western blot/immunodetection, using antibody specific for the LRP, for the WBLRP protein. To quantitate the lysine content in the transgenic seeds, total protein will be extracted from the seeds and its amino acid composition determined. Comparison of the lysine contents between the transgenic and control (untransformed) seeds should reveal the enhancement of the lysine content in the transgenic seeds.

Based on the foregoing disclosure, variations and modifications on the foregoing embodiments are within the ability of one of ordinary skill in the art, and such variations and modifications do not depart from the scope of the present invention as described in the following claims.

Samuel S. M. Sun, University of Hawaii, USA; Liwen Xiong, Beijing Vegetable Research Centers, China; and Jing Yuxiang & Bolin Lau, Institute of Botany, China.

What is claimed is:

1. A recombinant nucleic acid in isolated and purified form which nucleic acid comprises a nucleotide sequence encoding a winged bean lysine-rich protein (WBLRP), wherein said protein (a) has the amino acid sequence set forth in SEQ ID NO:2 or (b) is encoded by a nucleotide sequence that hybridizes under stringent conditions to a nucleotide sequence complementary to that which encodes the protein of SEQ ID NO:2 and wherein said protein is naturally expressed only in the developing seeds and its expression is not related to pathogen activity or wounding.

2. The nucleic acid of claim 1 wherein said WBLRP has the amino acid sequence set forth in SEQ ID NO:2.

3. The nucleic acid of claim 1 which is DNA.

4. The nucleic acid of claim 1 wherein said encoding nucleotide sequence is operably linked to heterologous nucleotide sequences that are selected from the group consisting of plant promoters, plant virus promoters and T-DNA promoters.

5. The nucleic acid of claim 3 wherein said encoding nucleotide sequence is operably linked to heterologous nucleotide sequences that are selected from the group consisting of plant promoters, plant virus promoters and T-DNA promoters.

6. A plant cell transformed to include the nucleic acid of claim 1 as a heterologous insertion.

7. The recombinant nucleic acid of claim 1, wherein lysine is the most abundant amino acid in the encoded WBLRP.

8. The recombinant nucleic acid of claim 1, wherein lysine constitutes about 10% in molar ratio of the amino acids of the encoded WBLRP.

9. An isolated nucleic acid that is fully complementary to the nucleotide sequence set forth in SEQ ID NO:1.

10. A recombinant DNA molecule comprising an expression system, which expression system comprises a nucleotide sequence encoding WBLRP, wherein said encoding sequence is under the transcriptional and/or translational control of regulatory sequences heterologous to said WBLRP-encoding nucleotide sequence, and wherein said protein (a) has the amino acid sequence set forth in SEQ ID NO:2 or (b) is encoded by a nucleotide sequence that hybridizes under stringent conditions to a nucleotide sequence complementary to that which encodes the protein of SEQ ID NO:2 and said protein is naturally expressed only in the developing seeds and its expression is not related to pathogen activity or wounding.

11. The DNA molecule of claim 10 wherein said WBLRP has the amino acid sequence set forth in SEQ ID NO:2.

12. The DNA molecule of claim 10 wherein said regulatory sequences comprise a nopaline synthase promoter, an octopine synthase promoter, a pea small subunit RUBP carboxylase promoter, a soybean small subunit RUBP carboxylase promoter, a maize Zein promoter, a wheat chlorophyll A/B binding protein promoter, a soybean 7S-alpha'-conglycinin promoter, a soybean glycinin G2 promoter, a soybean heat shock promoter, or a French bean phaseolin promoter.

13. A plant cell transformed to include the DNA molecule of claim 10 as a heterologous insertion.

14. A plant cell transformed to include the DNA molecule of claim 11 as a heterologous insertion.

15. A plant cell transformed to include the DNA molecule of claim 12 as a heterologous insertion.

16. A plant comprising the cell of claim 13.

17. A plant comprising the cell of claim 14.

18. A plant comprising the cell of claim 15.

* * * * *